United States Patent [19]

Schönafinger et al.

[11] Patent Number: 5,374,640
[45] Date of Patent: Dec. 20, 1994

[54] PYRIDYL-1,2,5-OXADIAZOLECARBOXA-MIDE-2-OXIDES

[75] Inventors: Karl Schönafinger, Alzenau; Helmut Bohn, Schöneck, both of Germany

[73] Assignee: Cassella Akliengesellschaft, Frankfurt, Germany

[21] Appl. No.: 67,561

[22] Filed: May 25, 1993

[30] Foreign Application Priority Data

Jun. 5, 1992 [DE] Germany .................. 4218582

[51] Int. Cl.⁵ .................. A61K 31/44; C07D 413/04
[52] U.S. Cl. .................. 514/340; 546/277
[58] Field of Search .................. 546/277; 514/340

[56] References Cited

U.S. PATENT DOCUMENTS 4,356,178  10/1982  Schonafinger et al. ............ 514/212
4,416,893  11/1983  Schonafinger et al. ............ 514/362

FOREIGN PATENT DOCUMENTS 1173034  8/1984  Canada .
054873   6/1982  European Pat. Off. .
0075141  3/1983  European Pat. Off. .
498137  12/1970  Switzerland .
498856  12/1970  Switzerland .

OTHER PUBLICATIONS

CA 118 (25): 254819j Ivanuv et al. 1992.
Liebigs Ann. Chem., 1990, pp. 335–338.
Ann. Chim. (Rome) 1968, vol. 58, pp. 200–212.
"Nitric Oxide" by Burnett et al., Science, Vo. 257, (1992), pp. 401, 403.
"Biological Roles of Nitric Oxide" by Snyder et al., Medicine Scientific American, May 1992, pp. 22–29.
Chemical Abstract, vol. 105 (1986), Abstract No. 114403a.

*Primary Examiner*—Jane T. Fan
*Attorney, Agent, or Firm*—Perman & Green

[57] ABSTRACT

The present invention relates to pyridyl-1,2,5-oxadiazolcarboxamide-2-oxides of the general formula I

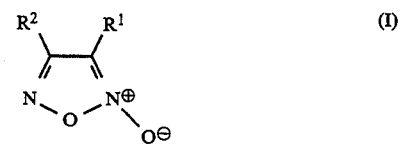

in which one of the radicals $R^1$ and $R^2$ represents pyridyl and the other represents

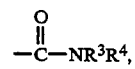

and $R^3$ and $R^4$ are defined as indicated in claim 1, processes for their preparation and their use.

8 Claims, No Drawings

PYRIDYL-1,2,5-OXADIAZOLECARBOXAMIDE-2-OXIDES

BACKGROUND OF THE INVENTION

1. Field of the Invention

The present invention relates to pyridyl-1,2,5-oxadiazolecarboxamide-2-oxides, processes for their preparation and their use.

2. Discussion of the Prior Art

Various 1,2,5-oxadiazolecarboxamide-2-oxides are already known and described, for example, in EP-B 054,872 and EP-B 054,873. However, pyridyl-substituted compounds of this class have not been described hitherto.

SUMMARY OF THE INVENTION

The present invention relates to pyridyl-1,2,5-oxadiazolecarboxamide-2-oxides of the general formula I

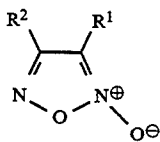

in which one of the radicals $R^1$ and $R^2$ represents pyridyl and the other represents

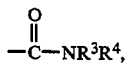

where $R^3$ and $R^4$ independently of one another denote hydrogen, $(C_1-C_6)$-alkyl, $(C_5-C_7)$-cycloalkyl, $-(CH_2)_n-NR^5R^6$, $-(CH_2)_n-OR^5$, $-(CH_2)_m-COOR^5$, $-CH(Alk)-COOR^5$, $-(CH_2)_m-CONR^5R^6$, $-CH(Alk)-CONR^5R^6$,

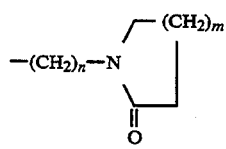

$-(CH_2)_m$-aryl or $-(CH_2)_m$-heteroaryl, or $R^3$ and $R^4$, together with the nitrogen atom bonding them, form a heterocycle;

$R^5$ and $R^6$ independently of one another denote hydrogen, $(C_1-C_6)$-alkyl, $(C_5-C_7)$-cycloalkyl, benzyl or phenethyl;

Alk denotes $(C_1-C_6)$-alkyl, and n represents 2, 3 or 4 and m represents 0, 1, 2 or 3, and their pharmacologically acceptable acid addition compounds.

The $(C_1-C_6)$-alkyl groups representing $R^3$, $R^4$, $R^5$, $R^6$ or Alk can be straight-chain or branched. Examples are methyl, ethyl, n-propyl, i-propyl, n-butyl, i-butyl, sec-butyl, tert-butyl or hexyl.

$(C_5-C_7)$-cycloalkyl representing $R^3$, $R^4$, $R^5$ or $R^6$ preferably denotes cyclopentyl or cyclohexyl.

In the $-(CH_2)_m$-aryl group representing $R^3$ or $R^4$, aryl is preferably 6- to 14-membered. Preferred $-(CH_2)_m$-aryl radicals are phenyl, benzyl and phenylethyl.

In the $-(CH_2)_m$-heteraryl group representing $R^3$ or $R^4$, heteraryl is preferably 5- to 7-membered and is derived, for example, from pyrrole, pyrrolidine, imidazole, pyridine, piperidine, morpholine or piperazine.

The aryl and heteraryl groups can optionally also be monosubstituted or polysubstituted. Suitable substituents are, for example, $(C_1-C_4)$-alkyl, $(C_1-C_4)$-alkoxy, amino, $(C_1-C_4)$alkylamino, di-$(C_1-C_4)$-alkylamino, $(C_1-C_6)$-alkanoylamino, halogen, preferably fluorine, chlorine or bromine, hydroxyl, nitro or cyano.

A heterocycle formed from $R^3$, $R^4$ and the nitrogen atom bonding them is, for example, pyrrolidine, piperidine, morpholine or piperazine, where the second nitrogen atom in the piperazine can also be substituted by a radical $R^5$.

$R^3$ and $R^4$ independently of one another preferably denote hydrogen or $(C_1-C_6)$-alkyl. Moreover, it is preferred if $R^3$ denotes $-(CH_2)_nN((C_1-C_6)$-alkyl$)_2$ and $R^4$ denotes hydrogen. Particularly preferably, $R^3$ denotes methyl and $R^4$ denotes hydrogen. The pyridyl radical representing $R^1$ or $R^2$ can be bonded via the 2-, 3- or 4-position. Pyrid-3-yl is preferred.

The compounds of the general formula I can be prepared, for example, by oxidising a compound of the general formula II

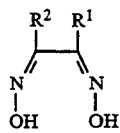

in which $R^1$ and $R^2$ are defined as indicated above.

The oxidising agents which can be employed here are conventional reagents such as, for example, halogens, alkali metal hypochlorites, lead(IV)acetate, iron(III) salts such as, for example, potassium ferricyanide, or nitrous gases, such as, for example, $N_2O_4$. The reaction is preferably carried out in a solvent, such as, for example, water, an alcohol, an ether, ethyl acetate, methylene chloride, cyclohexane, DMF, DMSO, benzene, toluene or chlorobenzene, at temperatures from $-10°$ C. to $50°$ C., preferably from $-5°$ C. to $25°$ C.

In the said oxidation, the compounds of the general formula I are as a rule obtained in the form of isomer mixtures. These can be separated, however by known methods such as recrystallisation or chromatographic methods, in particular column chromatography.

Isomer mixtures are also obtained when a pure isomer is heated on its own or in an inert solvent to temperatures from $50°$ to $200°$ C. or photolysed at $0°$ to $50°$ C. By separation of the mixture obtained in this way, it is thus possible to convert one isomer into the other.

The compounds of the general formula II can be prepared by reaction of compounds of the general formula III

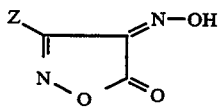

with an amine $HNR^3R^4$, where Z denotes pyridyl and $R^3$ and $R^4$ are defined as indicated above. The reaction is preferably carried out in an inert solvent at temperatures from 0° to 50° C.

The preparation of the compound of the formula III is described in Ann. Chim. (Rome) (1968), 58(2), 189–199, and in Ann. Chim. (Rome) (1959), 49, 2083–2088.

An alternative process for the preparation of compounds of the general formula I according to the invention consists in reacting a compound of the general formula IV

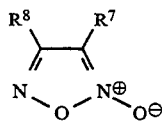   (IV)

in which one of the radicals $R^7$ and $R^8$ represents pyridyl and the other represents a reactive acid group, such as, for example,

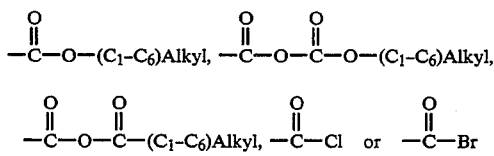

with an amine $HNR^3R^4$, in which $R^3$ and $R^4$ are defined in indicated above.

The reaction is advantageously carried out in the presence of a base which neutralises the acids formed. Preferred bases are alkali metal carbonates, such as sodium hydrogen carbonate or potassium hydrogen carbonate or sodium carbonate or potassium carbonate, alkali metal hydroxides, such as sodium hydroxide, potassium hydroxide or lithium hydroxide, alkali metal alkoxides, such as sodium methoxide or potassium methoxide, sodium ethoxide or potassium ethoxide or potassium tert-butoxide, alkali metal hydrides, such as sodium hydride or potassium hydride, alkali metal amides, such as sodium amide or lithium diisopropylamide or organic bases such as pyridine or triethylamine. These bases are preferably employed in molar amounts. Suitable solvents are, for example, ether, THF, alcohols, toluene, DMF and DMSO. The temperatures are 0° to 100° C., preferably 0° to 50° C.

If appropriate, the compounds of the general formula I according to the invention prepared by one of the processes above can be converted into other compounds of the general formula I according to the invention by modification of the substituents.

For example, the side chain —CO—NH—C(CH$_2$)$_m$COOR$^5$ can be converted by reaction with an amine HNR$^5$R$^6$ into the side chain —CO—NH—(CH$_2$)$_m$CONR$^5$R$^6$. The same is possible with the side chain —CO—NH—CH(Alk)—COOR$^5$.

By the process indicated above, compounds of the general formula Ia

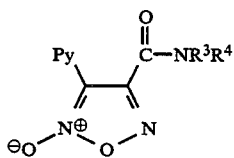   (Ia)

and of the general formula Ib

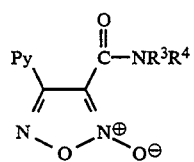   (Ib)

according to the invention, for example, can be prepared in which Py represents a 2-, 3- or 4-pyridyl radical and —NR$^3$R$^4$ in each case represents:

—NH$_2$;   —NHCH$_3$;   —NHCH$_2$CH$_3$;
—NH(CH$_2$)$_2$CH$_3$;   —NH(CH$_2$)$_3$CH$_3$;
—NH(CH$_2$)$_4$CH$_3$;   —NH(CH$_2$)$_5$CH$_3$;   —NHcycloC$_6$H$_{11}$;   —NHcycloC$_5$H$_9$;   —NH(CH$_2$)$_2$N(CH$_3$)$_2$;
—NH—(CH$_2$)$_2$N(CH$_2$CH$_3$)$_2$;
—NH(CH$_2$)$_2$N(CH$_2$CH$_2$CH$_2$CH$_3$)$_2$;   —NH—(CH$_2$)$_2$N(CH(CH$_3$)$_2$)$_2$;   —NH—(CH$_2$)$_2$NHCH(CH$_3$)$_2$;   —NH—(CH$_2$)$_2$NHcycloC$_6$H$_{11}$;   —NH(CH$_2$)$_3$N(CH$_2$CH$_3$)$_2$;

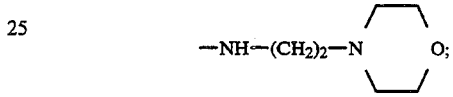

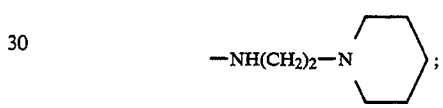

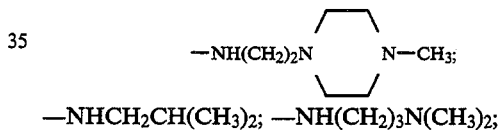

—NHCH$_2$CH(CH$_3$)$_2$;   —NH(CH$_2$)$_3$N(CH$_3$)$_2$;

—NHCH$_2$C(CH$_3$)$_3$;   —NH(CH$_2$)$_4$N(CH$_3$)$_2$;
—NH(CH$_2$)$_3$NHcyclolC$_6$H$_{11}$;
—NH(CH$_2$)$_3$NHC(CH$_3$)$_3$;   —NH(CH$_2$)$_2$OCH$_3$;
—NH(CH$_2$)$_2$OCH$_2$CH$_3$;   —NH(CH$_2$)$_2$O(OH$_2$)CH$_3$;
—NH(CH$_2$)$_2$OCH(CH$_3$)$_2$;   —NH(CH$_2$)$_3$OCH$_3$;
—NH(CH$_2$)$_4$OCH$_3$;   —NH(CH$_2$)$_3$OCH$_2$CH$_3$;
—NH(CH$_2$)$_3$O(CH$_2$)$_3$CH$_3$;   —NH(CH$_2$)$_2$OH;
—NH(CH$_2$)$_3$OH;   —NH(CH$_2$)$_2$OcycloC$_5$H$_9$;
—NH(CH$_2$)$_2$phenyl;   —NHCH$_2$phenyl;   —NH(CH$_2$)$_3$phenyl);   —NH(CH$_2$)$_2$(3,4-di-OCH$_3$-phenyl);
—NHCH$_2$(4-OCH$_3$-phenyl);   —NHCH$_2$COOCH$_3$;
—NHCH$_2$COOCH;   —NHCH$_2$COOCH$_2$CH$_3$;
—NHCH$_2$CONH$_2$;   —NHCH$_2$CONHCH$_3$;   —NHCH$_2$CON(CH$_2$CH$_3$)$_2$;   —NH(CH$_2$)$_2$COOH;   —NH(CH$_2$)$_2$COOCH(CH$_3$)$_2$;   —NH(CH$_2$)$_2$CONHCH$_2$CH$_3$;
—NH(CH$_2$)$_3$COOH;   —NH(CH$_2$)$_3$CONH(CH$_2$)$_3$CH$_3$;
—NH(CH$_2$)$_3$CONH$_2$;   —NH(CH$_2$)$_3$COOCH$_2$CH$_3$;
—NHCH$_2$(3-pyridyl);   —NH(CH$_2$)$_2$(4-pyridyl);
—NH(CH$_2$)$_2$(4-imidazolyl);   —NHCH$_2$(2-pyridyl);
—NHCH(CH$_3$)COOH;   —NHCH(CH(CH$_3$)$_2$)CONH$_2$;
—NHCH(CH$_2$CH(CH$_3$)$_2$)CON(CH$_3$)$_2$;
—NH(CH$_2$)$_2$(2-oxopyrrolidin-1-yl) or —NH(CH$_2$)$_3$(2-oxopyrrolidin-1-yl).

Compounds of the general formula I according to the invention which contain a basic group can form salts with inorganic or organic acids. Suitable acids for the formation of pharmacologically acceptable acid addition salts are, for example: hydrogen chloride, hydrogen bromide, naphthalenedisulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulfamic, phenylpropionic, gluconic, ascorbic, isonicotinic, methanesulphonic, p-toluenesulphonic, citric or adipic acid. The acid addition salts can be prepared in the customary manner by combination of the components, expediently in a suitable solvent or diluent.

The compound of the general formula I and their pharmacologically acceptable acid addition salts have useful pharmacological properties. In the guinea-pig potassium-depolarised pulmonary artery model, they lead at low concentrations to a long-lasting relaxation. This action can be inhibited by oxyhaemoglobin, which points to an NO-mediated mechanism. Nitrogen monoxide leads, as an activator of guanylate cyclase, to an increase in cyclic guanosine monophosphate, which causes a relaxation in the smooth muscle and antiadhesive and antiaggregatory actions in the blood platelets. Nitrogen monoxide is additionally also crucially involved in learning processes, in the regulation of kidney function, in immune defence, in septic shock and in erectile dysfunctions. The compounds according to the invention can thus be employed in the said indications. Above all, however, NO donors have proven suitable for the treatment and prophylaxis of angina pectoris.

The compounds of the general formula I and their pharmacologically acceptable acid addition salts can therefore be administered in humans as medicines per se, in mixtures with one another or in the form of pharmaceutical preparations which permit enteral or parenteral use and which as active constituent contain an effective dose of at least one compound of the general formula I or of an acid addition salt thereof, in addition to customary pharmaceutically innocuous excipients and additives.

The medicines can be administered orally, for example in the form of pills, tablets, coated tablets, sugar-coated tablets, hard and soft gelatin capsules, solutions, syrups, emulsions or suspensions, or aerosol mixtures. However, administration can also be carried out rectally, for example in the form of suppositories, or parenterally, for example in the form of injection solutions, or percutaneously, for example in the form of ointments or tinctures.

For the production of the pharmaceutical preparations, pharmaceutically inert inorganic or organic excipients can be used. For the preparation of pills, tablets, sugar-coated tablets and hard gelatin capsules, lactose, maize starch or derivatives thereof, talc, steric acid or its salts, etc., for example, can be used. Excipients for soft gelatin capsules and suppositories are, for example, fats, waxes, semi-solid and liquid polyols, natural or hardened oils, etc. Suitable excipients for the production of solutions and syrups are, for example, water, sucrose, invert sugar, glucose, polyols, etc. Suitable excipients for the production of injection solutions are, for example, water, alcohols, glycerol, polyols or vegetable oils.

In addition to the active compounds and excipients, the pharmaceutical preparations can also contain additives, such as, for example, fillers, extenders, disintegrants, binders, lubricants, wetting agents, stabilisers, emulsifiers, preservatives, sweeteners, coloarants, flavourings or araomatisers, buffer substances, and also solvents or solubilisers or agents for achieving a depot effect, as well as salts for changing the osmotic pressure, coating agents or antioxidants. They can also contain two or more compounds of the general formula I or their pharmacologically acceptable acid addition salts and additionally other therapeutically active substances.

Other therapeutically active substances of this type are, for example: $\beta$-receptor blockers, such as, for example, propranolol, pindolol, metoprolol; vasocilators, such as, for example, carbocromen; tranquillisers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, ramipril, prazosin, clonidine, rauwolfia alkaloids; agents which reduce the fatty acid level in the blood, such as, for example, bezafibrate, fenofibrate; and agents for thrombosis prophylaxis, such as, for example, phenprocoumon.

The compound of the general formula I, their pharmacologically acceptable acid addition salts and pharmaceutical preparations which contain the compounds of the general formula I or their pharmacologically acceptable acid addition salts as active compounds can be used in humans in the control or prevention of disorders of the cardiovascular system, for example as antihypertensive medicines in the various forms of high blood pressure, and in the control or prevention of angina pectoris, etc. Moreover, they can also be employed for the treatment of erectile dysfunctions. The dose can vary within wide limits and is to be adapted to the individual conditions in each individual case. In general, in the case of oral administration a daily dose of about 0.5 to 100 mg, preferably 1 to 20 mg, is adequate per human individual. In the case of other administration forms, the daily dose, because of the good adsorption of the active compounds, is also in similar ranges of amounts, i.e. in general also 0.5 to 100 mg/human. The daily dose is normally divided into several, for example 2 to 4, part administrations.

EXAMPLES 1a) 4-Hydroximino-3-(pyrid-3-yl)isoxazol-5-one

A suspension of 57 g of 3-(pyrid-3-yl)isoxazol-5-one in 50 ml of water and 350 ml of glacial acetic acid is treated dropwise at 15° C. with a solution of 27 g of sodium nitrite in 60 ml of water. After 4 hours, the precipitate is filtered off with suction, washed with water and dried.

Yield: 53 g M.p.: 192° C. (dec.)

b) General procedure for the preparation of 3-(pyrid-3-yl)-2,3-dioximinopropionamides A solution of 0.05 mold of 4-hydroximino-3-(pyrid-3-yl)isoxazol-5-one in 50 ml of methanol is treated at room temperature with an amine $HNR_3R_4$ (0.055 mol) and left alone for several hours to days. The precipitate is filtered off with suction and washed with methanol. If a precipitate does not deposit, the mixture is concentrated in a rotary evaporator and the residue is recrystallised from a suitable solvent or purified by column chromatography (silica gel). The following are prepared in this manner:

1. N-Methyl-3-(pyrid-3-yl)-2,3-dioximinopropionamide
   M.p.: 153° C. (dec.)
2. N-Hexyl-3-(pyrid-3-yl)-2,3-dioximinopropionamide
   M.p.: 201° C. (dec.)
3. N-Benzyl-3-(pyrid-3-yl)-2,3-dioximinopropionamide
   M.p.: 140° C. (dec.)
4. N-Propyl-3-(pyrid-3-yl)-2,3-dioximinopropionamide
   M.p.: 184° C. (dec.) p 5. N-(2-diethylaminoethyl)-2,3-dioximinopropionamide
   M.p.: 174° C. (dec.)

c) General procedure for the preparation of pyrid-3-yl-1,2,5-oxadiazolecarboxamide-N-oxides A mixture of 0.02 mol of a compound according to 1b) and 20 ml of water is treated with 2N sodium hydroxide solution until everything has gone into solution. After cooling in an ice bath, a 14% strength chlorine bleach liquor (0.022 mol) is added dropwise and the precipitate is filtered off with suction after 15 minutes. If an oil separates, the product is extracted with ethyl acetate or methylene chloride. The solid or the oil obtained is worked up by column chromatography (silica gel, eluent: cyclohexane/ethyl acetate), two isomeric products being obtained which can be converted into the hydrochlorides by dissolving in ethyl acetate/ether mixtures containing hydrochloric acid. The following are prepared in this manner:

1. N-Methyl-3-(pyrid-3-yl)-1,2,5-oxadiazole-4-carboxamide-2-oxide
   M.p.: 189°-191° C.
2. N-Methyl-4-(pyrid-3-yl)-1,2,5-oxadiazole-3-carboxamide-2-oxide
   M.p.: 151°-153° C.
3. N-Hexyl-4-(pyrid-3-yl)-1,2,5-oxadiazole-3-carboxamide-2-oxide
   M.p.: Oil
4. N-Hexyl-4-(pyrid-3-yl)-1,2,5-oxadiazole-3-carboxamide-2-oxide hydrochloride
   M.p.: 143° C. (dec.)
5. N-Benzyl-4-(pyrid-3-yl)-1,2,5-oxadiazole-3-carboxamide-2-oxide
   M.p.: 85°-87° C.
6. N-Benzyl-3-(pyrid-3-yl)-1,2,5-oxadiazole-4-carboxamide-2-oxide
   M.p.: 135°-137° C.
7. N-Propyl-4-(pyrid-3-yl)-1,2,5-oxadiazole-3-carboxamide-2-oxide
   M.p.: 62°-63° C.
8. N-(2-Diethylaminoethyl)-4-(pyrid-3-yl)-1,2,5-oxadiazole-3-carboxamide-2-oxide
   M.p.: Oil
9. N-(2-Methoxyethyl)-4-(pyrid-3-yl)-1,2,5-oxadiazole-3-carboxamide-2-oxide hydrochloride
   M.p.: 145°-148° C.
10. N-(2-Methoxyethyl)-3-(pyrid-3-yl)-1,2,5-oxadiazole-4-carboxamide-2-oxide
    M.p.: 84°-86° C.
11. N-(2-Diethylaminoethyl)-3-(pyrid-3-yl)-1,2,5-oxadiazole-4-carboxamide-2-oxide
    Oil
12. N-(2-Hydroxyethyl)-3-(pyrid-3-yl)-1,2,5-oxadiazole-4-carboxamide-2-oxide
    M.p.: 178°-179° C.
13. N-(2-Hydroxyethyl)-4-(pyrid-3-yl)-1,2,5-oxadiazole-3-carboxamide-2-oxide
    M.p.: 147°-149° C.
14. N-(3-Imidazol-1-ylpropyl)-3-(pyrid-3-yl)-1,2,5-oxadiazole-4-carboxamide-2-oxide
    M.p.: 104°-106° C.
15. N-(3-Imidazol-1-ylpropyl)-4-(pyrid-3-yl)-1,2,5-oxadiazole-3-carboxamide-2-oxide
    M.p.: 88°-89° C.
16. N-(Aminocarbonylmethyl)-4-(pyrid-3-yl)-1,2,5-oxadiazole-3-carboxamide-2-oxide
    M.p.: 197°-198° C.
17. N-(2-Diisopropylaminoethyl)-4-(pyrid-3-yl)-1,2,5-oxadiazole-3-carboxamide-2-oxide hydrochloride
    M.p.: 191° C. (dec.)
18. N-(2-Diisopropylamnoethyl)-3-(pyrid-3-yl)-1,2,5-oxadiazole-4-carboxamide-2-oxide hydrochloride
    M.p.: 191° C. (dec.)
19. 4-(Pyrid-3-yl)-1,2,5-oxadiazole-3-pyrrolidin-1-yl)-carbonyl-2-oxide
    M.p.: 112°-114° C.
20. N-(2-Diethylaminoethyl)-4-(pyrid-3-yl)-1,2,5-oxadiazole-3-carboxamide-2-oxide hydrofumarate
    M.p.: 122°-123° C.
21. N-(3-Dimethylaminopropyl)-4-(pyrid-3-yl)-1,2,5-oxadiazole-3-carboxamide-2-oxide
    Oil
22. N-(2-Diethylaminoethyl)-4-(pyrid-2-yl)-1,2,5-oxadiazole-3-carboxamide-2-oxide hydrofumarate
    M.p.: 148°-151° C. (dec.)
23. N-(3-Diethylaminopropyl)-3-(pyrid-3-yl)-1,2,5-oxadiazole-4-carboxamide-2-oxide
    Oil
24. N-Methyl-3-(pyrid-4-yl)-1,2,5-oxadiazole-4-carboxamide
    M.p.: 195°-196° C.
25. N-Methyl-4-(pyrid-4-yl)-1,2,5-oxadiazole-3-carboxamide
    M.p.: 155°-156° C.
26. N-(3-Imidazol-1-ylpropyl)-4-(pyrid-4-yl)-1,2,5-oxadiazole-3-carboxamide-2-oxide hydrofumarate
    M.p.: 151° C. (dec.)
27. N-(3-Imidazol-1-ylpropyl)-3-(pyrid-4-yl)-1,2,5-oxadiazole-4-carboxamide-2-oxide hydrofumarate
    M.p.: 153° C. (dec.)
28. 3-(Pyrid-3-yl)-1,2,5-oxadiazole-4-carboxamide-2-oxide
    M.p.: 193° C. (dec.)

The pharmacological action of the compounds of the general formula I was determined by a modified method of Godfraind and Kaba (Arch. Int. Pharmacodyn. Ther. 196, (Suppl) 35 to 49, 1972) and by Schüman et al (Naunyn-Schmiedeberg's Arch. Pharmacol. 289, 409 to 418, 1975). In this method, spiral strips of the pulmonary artery of the guinea-pig are depolarised with 40 mmol/l of potassium after equiliberation in calcium-free Tyrode solution. An addition of 0.5 mmol/l of $CaCl_2$ then induces a contraction.

The relaxing action of the test substance is determined by cumulative addition in ½ log 10 graded concentrations. From the concentration-action curve (abscissa: —log mol/l test substance, ordinate: % inhibition of the maximum contraction, average value of 4 to 6 vessel strips), the concentration of the test substance is determined which inhibits the contraction by 50% (=$IC_{50}$, mol/l).

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Pyridyl-1,2,5-oxadiazolcarboxamide-2-oxides of the formula I

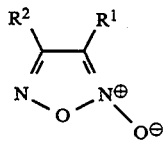

in which one of the radicals $R^1$ and $R^2$ represents pyridyl and the other represents

where $R^3$ and $R^4$ independently of one another denote hydrogen, $(C_1-C_6)$-alkyl, $(C_5-C_7)$-cycloalkyl, $-(CH_2)_n-NR^5R^6$, $-(CH_2)_n-OR^5$, $-(CH_2)_m-COOR^5$, $-CH(Alk)-COOR^5$, $-(CH_2)_m-CONR^5R^6$, $-CH(Alk)-CONR^5R^6$, $(CH_2)_m-(C_6-C_{14})$-Aryl;

$R^5$ and $R^6$ independently of one another denote hydrogen, $(C_1-C_6)$-alkyl, $(C_5-C_7)$-cycloalkyl, benzyl or phenethyl;

Alk denotes $(C_1-C_6)$-alkyl, and n represents 2, 3 or 4 and m represents 0, 1, 2 or 3, or a pharmacologically acceptable acid addition compounds thereof.

2. Pyridyl-1,2,5-oxadiazolecarboxamide-2-oxide of claim 1 wherein $R^3$ and $R^4$ independently of one another denote hydrogen or $(C_1-C_6)$-alkyl.

3. Pyridyl-1,2,5-oxadiazolecarboxamide-2-oxide of claim 1 wherein $R^3$ denotes methyl and $R^4$ denotes hydrogen.

4. Pyridyl-1,2,5-oxadiazolecarboxamide-2-oxide of claim 1 wherein $R^3$ denotes $-(CH_2)_nN((C_1-C_6)$-alkyl$)_2$ and $R^4$ denotes hydrogen.

5. Pyridyl-1,2,5-oxadiazolecarboxamide-2-oxide of claim 1 wherein the pyridyl radical representing $R^1$ or $R^2$ is pyrid-3-yl.

6. Pharmaceutical composition for the treatment of angina pectoris or hypertension characterized in that it contains an effective amount of pyridyl-1,2,5-oxadiazolecarboxamide-2-oxide of the formula I according to claim 1, or a pharmacologically acceptable acid addition salt thereof as active compound together with pharmaceutically acceptable excipient and additives.

7. Method for the treatment and control of angina pectoris which comprises administering to a host in need thereof an effective dose of a compound of the formula I according to claim 1.

8. Method for the treatment of hypertension which comprises administering to a host in need thereof an effective dose of a compound of the formula I according to claim 1.

* * * * *